(12) United States Patent
Traeger

(10) Patent No.: US 6,558,340 B1
(45) Date of Patent: May 6, 2003

(54) DIALYSIS MACHINE, IN PARTICULAR FOR HOME USE

(75) Inventor: Jules Traeger, Lyons (FR)

(73) Assignee: Valemont Participation Corp., Tortola (VG)

(*) Notice: Subject to any disclaimer, the term of this patent is extended or adjusted under 35 U.S.C. 154(b) by 0 days.

(21) Appl. No.: 09/719,790

(22) PCT Filed: Jun. 17, 1999

(86) PCT No.: PCT/IB99/01138
§ 371 (c)(1),
(2), (4) Date: Dec. 15, 2000

(87) PCT Pub. No.: WO99/65543
PCT Pub. Date: Dec. 23, 1999

(30) Foreign Application Priority Data

Jun. 17, 1998 (FR) .............................. 98 07871

(51) Int. Cl.[7] ............................................. A61M 37/00
(52) U.S. Cl. ................... 604/5.01; 604/4.01; 604/6.01; 604/6.09; 210/646; 210/645
(58) Field of Search ............... 604/5.01, 4.01, 604/6.01, 6.06, 6.09, 29, 30; 210/646, 645, 651, 636

(56) References Cited

U.S. PATENT DOCUMENTS

| | | | | |
|---|---|---|---|---|
| 4,024,059 A | * | 5/1977 | Sausse | 210/646 |
| 4,132,644 A | | 1/1979 | Kolberg | |
| 4,303,068 A | * | 12/1981 | Zelman | 128/214 B |
| 4,331,540 A | * | 5/1982 | Witsoe | 210/646 |
| 4,386,634 A | | 6/1983 | Stasz et al. | |
| 4,676,905 A | * | 6/1987 | Nagao et al. | 210/646 |
| 4,702,829 A | * | 10/1987 | Polaschegg et al. | 210/195.2 |
| 4,950,395 A | | 8/1990 | Richalley | |
| 5,004,548 A | * | 4/1991 | Richalley et al. | 210/646 |
| 5,230,341 A | * | 7/1993 | Polaschegg | 128/668 |
| 5,336,165 A | * | 8/1994 | Twardowski | 604/5 |
| 5,685,835 A | * | 11/1997 | Brugger | 604/5 |
| 5,685,988 A | * | 11/1997 | Malchesky | 210/646 |
| 5,733,457 A | * | 3/1998 | Hovland et al. | 210/636 |
| 5,863,421 A | * | 1/1999 | Peter, Jr. et al. | 210/134 |
| 5,938,634 A | * | 8/1999 | Packard | 604/29 |
| 5,944,684 A | * | 8/1999 | Roberts et al. | 604/5 |
| 6,074,359 A | * | 6/2000 | Keshaviah et al. | 604/29 |
| 6,187,199 B1 | * | 2/2001 | Goldau | 210/646 |
| 6,331,252 B1 | * | 12/2001 | El Sayyid et al. | 210/646 |

FOREIGN PATENT DOCUMENTS

WO          95/20985          1/1995

* cited by examiner

Primary Examiner—Ira S. Lazarus
Assistant Examiner—Tu Cam Nguyen
(74) Attorney, Agent, or Firm—Davis & Bujold, P.L.L.C.

(57) ABSTRACT

The invention concerns a dialysis machine (10) comprising a dialyzer (20) having a first inlet (21) and a first outlet (22) for the bloodstream, dialysate supply mechanism (25), an arterial line (16) connected between the patent's arteriovenous fistula and the dialyzer, a venous line (17) connected between the arteriovenous fistula and the dialyzer, a pump (28) coupled with the arterial line, a dialysate supply line (31), connected between the dialysate supply mechanism and the dialyzer, a dialysate evacuation line (33) connected between a dialysate recuperating container (27) and the dialyzer. The sterile dialysate bags are arranged in a chamber (26) under a gas pressure.

19 Claims, 6 Drawing Sheets

# DIALYSIS MACHINE, IN PARTICULAR FOR HOME USE

TECHNICAL REALM

The present invention concerns a dialysis machine, particularly for home use, comprising a dialyzer, for example, a hollow fiber type dialyzer, with a first blood circulation inlet and a first blood circulation outlet, a dialysate supply means, an arterial line connected between the patient's arteriovenous fistula and said first dialysis inlet, a venous line connected between said arteriovenous fistula and said first dialyzer outlet, a pump associated with said artery line, a dialysate inlet line connected between said dialysate supply means and a second dialyzer inlet, and a dialysate evacuation line connected between the dialysate collection container and a second dialysis outlet.

PRIOR ART

Chronic dialysis traditionally requires large quantities of dialysate. Approximately 120 liters of dialysate are necessary for proper diffusion exchange at the dialyzer membrane in order to purify the patient's blood.

Dialysis is currently performed three times a week in a hospital for about four hours and requires complex machinery, particularly water treatment equipment to provide water of sufficiently high quality in terms of mineral level and bacterial count. This purified water is added to a concentrate to make the amount of dialysate needed. Despite this, and despite daily disinfection of the dialysis machines, the risk of contamination remains high.

The fact that the patient is treated for relatively long periods of time is a major inconvenience. The patient becomes hypercatabolic between sessions, and treatment necessitates a long, tiring intervention and complex equipment, primarily due to the large quantities of dialysate to be prepared. The machinery that performs hemodialysis in hospital settings is very cumbersome and impossible for an non-qualified person to use. For these reasons it is very difficult to allow a patient connect himself or herself without assistance and medical supervision. Current equipment is so complex that technicians must always be nearby for maintenance.

Dialysis machines of the type described in the preamble for home use are known in the art, particularly in U.S. Pat. No. 4,950,395. This document describes a very elementary dialysis apparatus which operates on the basis of gravity and blood pressure, with a pump attached in series on the dialysate inlet line. The apparatus has grip or clamps attached to the various lines to regulate flow during the dialysis session using a flowmeter. There are considerable variations in dialysate flow between the beginning and the end of the session, which has a marked effect on dialysis performance. Moreover, regulating the flow is relatively difficult; the assistance of a third person is required.

International application published as No. WO-95 20 985 concerns a dialysis apparatus mainly consisting of a chamber, a reversible pump to pressurize or depressurize the chamber, a heated pouch for sterile dialysate, and a used dialysate evacuation pouch placed inside the chamber and joined with a T connector to a catheter connected to the peritoneum of the patient. A valve device permits the flow of liquid to be selectively established between the catheter and one of the pouches. When the pouch is depressurized, sterile dialysate flows into the heated pouch from the supply pouches, and used dialysate is evacuated from the patient into the evacuation pouch. When the chamber is pressurized, sterile, heated dialysate flows into the patient from the heated pouch and used dialysate flows into a collection container. However, this dialysis apparatus is designed only for use in peritoneal dialysis.

U.S. Pat. No. 4,132,644 has as its object a dialysis machine which recycles used dialysate using a peristaltic pump to generate dialysate flow and which requires regulation of dialysate flow during the session. The dialysate supply pouch is located inside a chamber sealed with variable pressure to modify pressure within the pouch and in the circuit, thereby regulating dialysate flow. This apparatus is difficult to use correctly and requires the assistance of a qualified person.

U.S. Pat. No. 4,386,634 has as its object an apparatus and a technique for preparing dialysate.

DESCRIPTION OF THE INVENTION

The present invention proposes overcoming the various disadvantages for chronic dialysis mentioned above by eliminating long treatment sessions in a hospital setting and substituting much shorter, daily sessions using smaller quantities of dialysate packaged in sterile bags, thereby eliminating the risk of the patient becoming hypercatabolic between two dialysis sessions; these sessions can take place at home without any medical assistance or supervision, as the dialysis machine can be operated without any complex manipulations. Another aim of the invention is to provide a simple, reliable dialysis machine, especially for use in acute dialysis where treatment is continuous, and also for performing hemodiafiltration when the machine is used for either chronic dialysis or acute dialysis.

These objectives are met by a dialysis machine such as the machine described in the preamble, characterized in that said dialysate supply means comprises at least one chamber in which there is at least one pouch containing sterile dialysate, said pouch being connected to said dialysate inlet line leading to the dialyzer, and a means for pressurizing said pouch to provoke the flow of dialysate into said inlet line.

According to a preferred embodiment of the dialysis machine used for acute dialysis, said supply means comprises at least two chambers, each containing at least one pouch of sterile dialysate, said two pouches being capable of separate pressurization by said pressurizing means, and at least two reserve pouches of sterile dialysate located outside said chambers, each connected to one of said respective pouches by a conduit. Said dialysis machine advantageously comprises a system for alternately clamping these conduits.

According to a particular embodiment of the dialysis machine used for hemodiafiltration, said supply means consists of at least one pouch of sterile dialysate located in a chamber and connected with an inlet line to said venous line.

Said pressurizing means preferably consists of at least one gas reservoir connected to said chamber. There may be at least one air compressor.

It is advantageous for said inlet line to be calibrated so that when there is a given pressure in the chamber, the liquid will flow at a constant given rate.

Preferably the dialysate inlet line leading to the dialyzer is calibrated so that when there is a predetermined pressure in the chamber, the dialysate will flow at a rate ranging essentially from 100 to 500 ml/minute and preferably from 100 to 250 ml/minute.

The dialysate inlet line advantageously has a flow restrictor to generate a predetermined loss of charge. This inlet line may consist at least partially of a reinforced calibrated tube having a constant section along a predetermined length.

According to a particular embodiment of the dialysis machine designed for hemodiafiltration, said pressurizing means advantageously maintains an interior pressure within the chamber that is sufficient to provoke the flow of dialysate through the inlet lines to a bubble trap and to the dialyzer, respectively. The inlet lines preferably are calibrated so that for a given predetermined pressure in the chamber, the liquid will flow at a constant given rate.

It is advantageous for the dialysis machine to comprise a volumetric device connected to the evacuation line and joining the second outlet of the dialyzer with the dialysate collection container. Said volumetric device may be a dialysate pump with an adjustable flow rate.

According to a preferred construction, the dialysis machine comprises a frame with a housing for said dialyzer, at least one chamber containing at least one pouch of sterile dialysate, said arterial line connected between the patient's artery and said first dialyzer inlet, said venous line connected between the patient's vein and said first dialyzer outlet, said pump coupled to said artery line, said sterile dialysate inlet line connected between said pouch of sterile dialysate and the second dialyzer inlet, said dialysate collection container, said dialysate evacuation line connected between said second dialyzer outlet and said collection container, said means for pressurizing the sterile dialysate pouch located within said chamber, and a folding cover attached to the frame.

According to a particular form of the dialysis machine designed for performing acute dialysis, said housing surrounds the two chambers which each contain at lest one pouch of sterile dialysate and said dialysis machine comprises a support integral with the frame for holding the pouches of reserve sterile dialysate. The support for the reserve pouches may consist of the cover.

SUMMARY OF THE DRAWINGS

The present invention will be better understood with reference to the following description of various preferred embodiments of a dialysis machine according to the invention and with reference to the attached drawings, provided as non-limiting examples, wherein.

PREFERRED EMBODIMENT OF THE INVENTION

Figure 1:
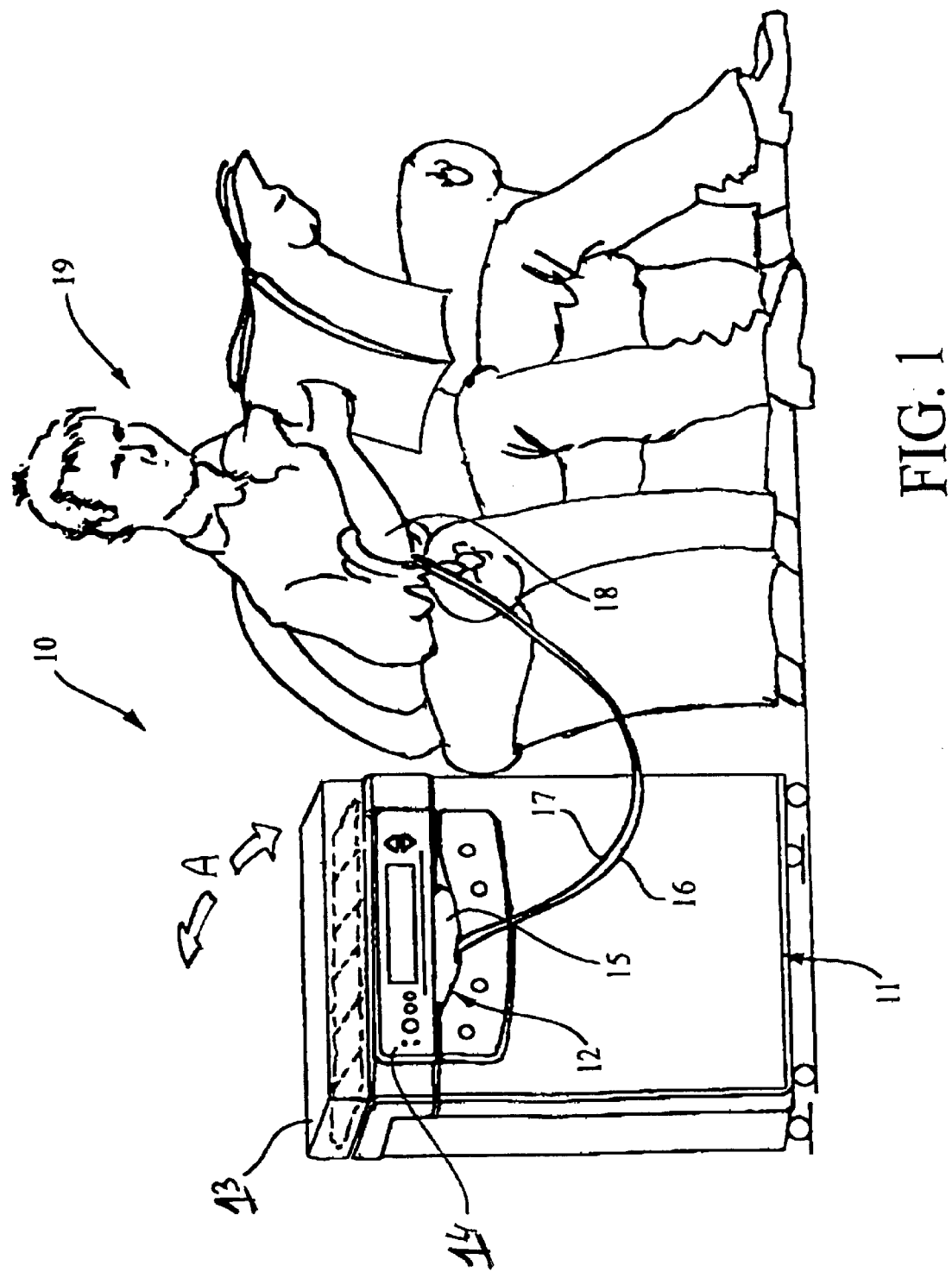
FIG. 1 is a schematic representation of a dialysis machine according to the invention being used on a patient requiring chronic dialysis.

Dialysis machine 10, as shown schematically in FIG. 1, essentially comprises a frame 11 defining a housing 12 with a folding cover 13 attached to it, as shown by arrows A. The front facade of the machine has a control panel 14 incorporating the control buttons necessary for simplified use by the patient himself or a person who is not necessarily highly qualified. There is an opening 15 formed in control panel 14 for the conduits called arterial line 16 and venous line 17 that connect to an arteriovenous fistula (not shown in detail) implanted in the forearm 18 of a patient 19. The mode shown in FIG. 1 concerns chronic dialysis where the patient must undergo regular dialysis, preferably daily. Because it is easy to manipulate and control, the machine of the invention allows the patient himself to perform the intervention. The control buttons on the panel could be supplemented or replaced by an automatic infrared light control or the like.

Figure 2A:
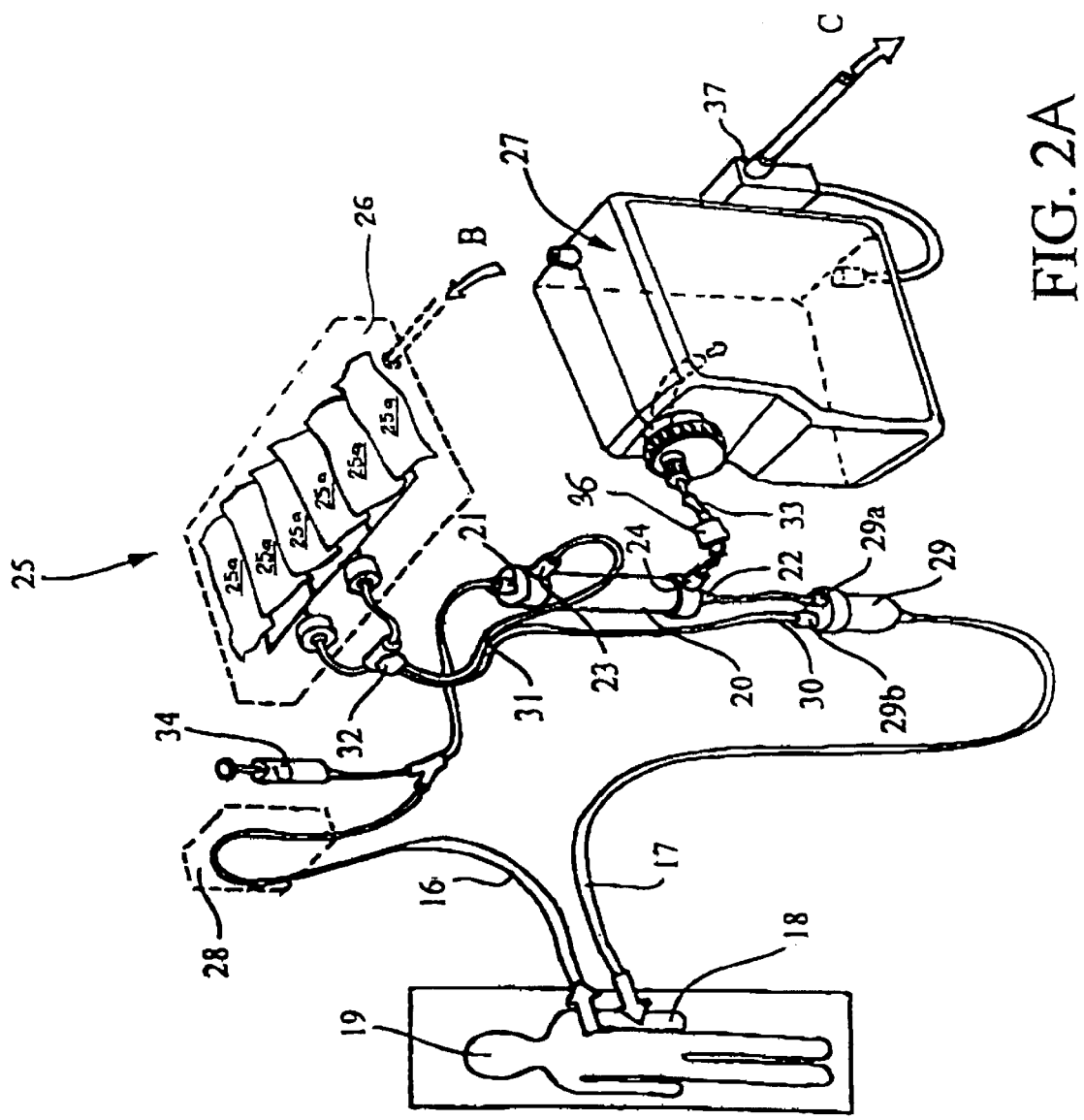
FIGS. 2A and 2B are schematic representations in perspective showing the essential components of the dialysis machine according to the invention, with two embodiments for performing chronic dialysis and acute dialysis, respectively.
Figure 2B:
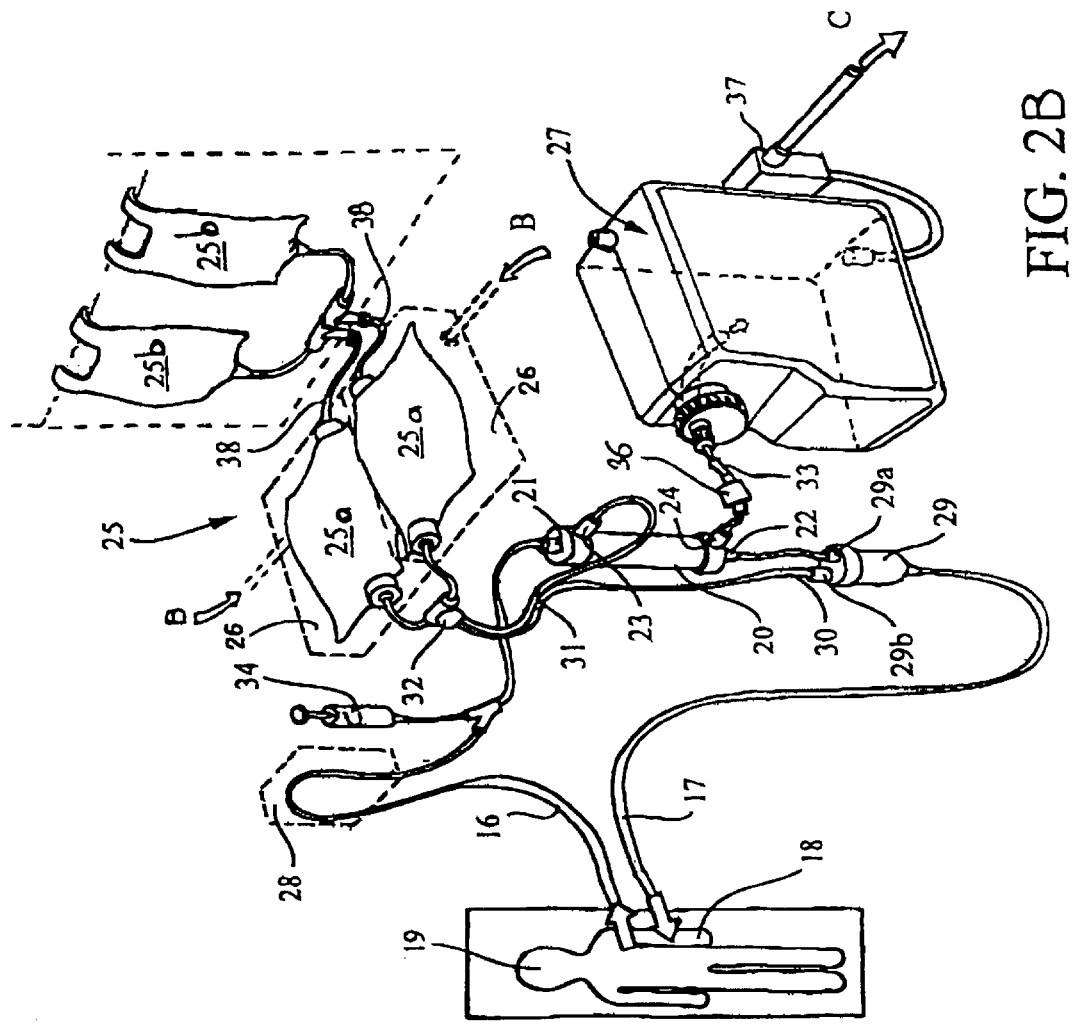
Figure 3A:
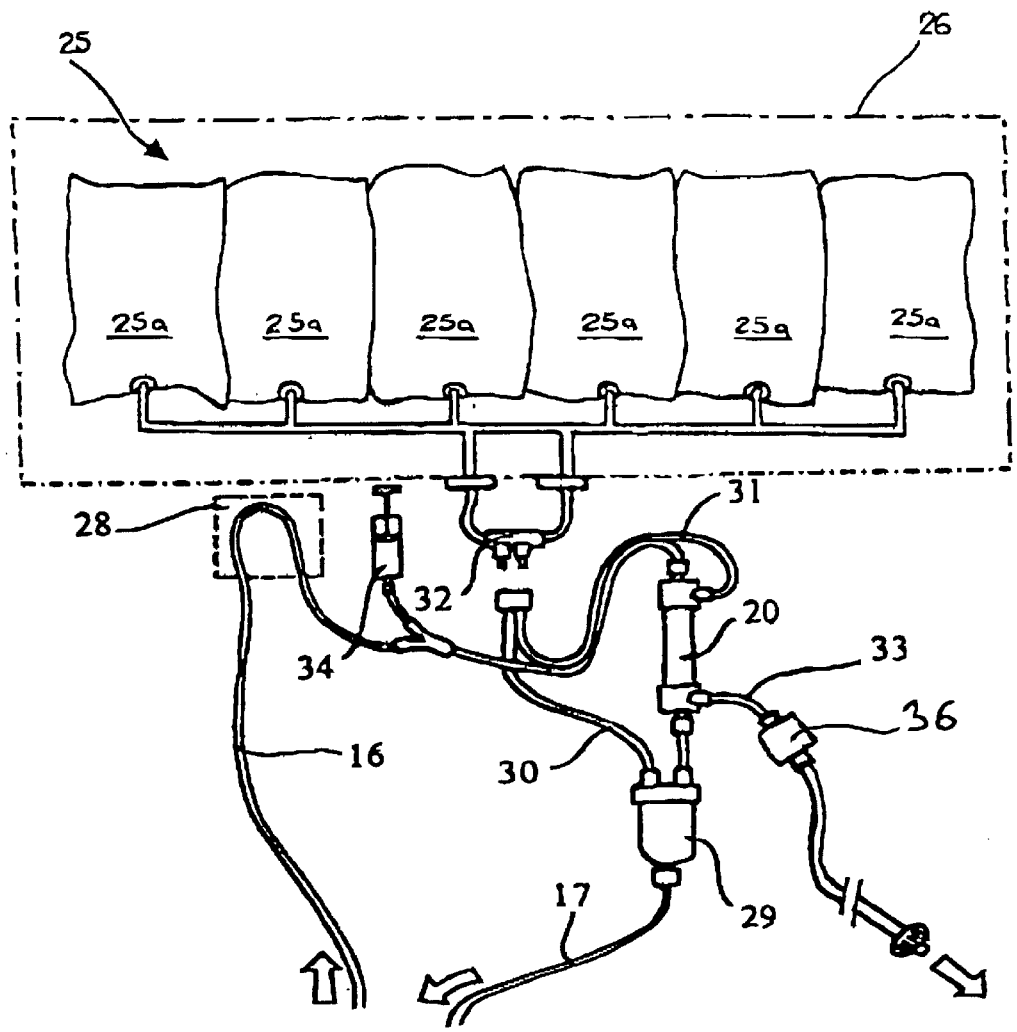
FIGS. 3A and 3B are exploded views of the various components of the dialysis machines corresponding to the two embodiments show in FIGS. 2A and 2B, respectively.
Figure 3B:
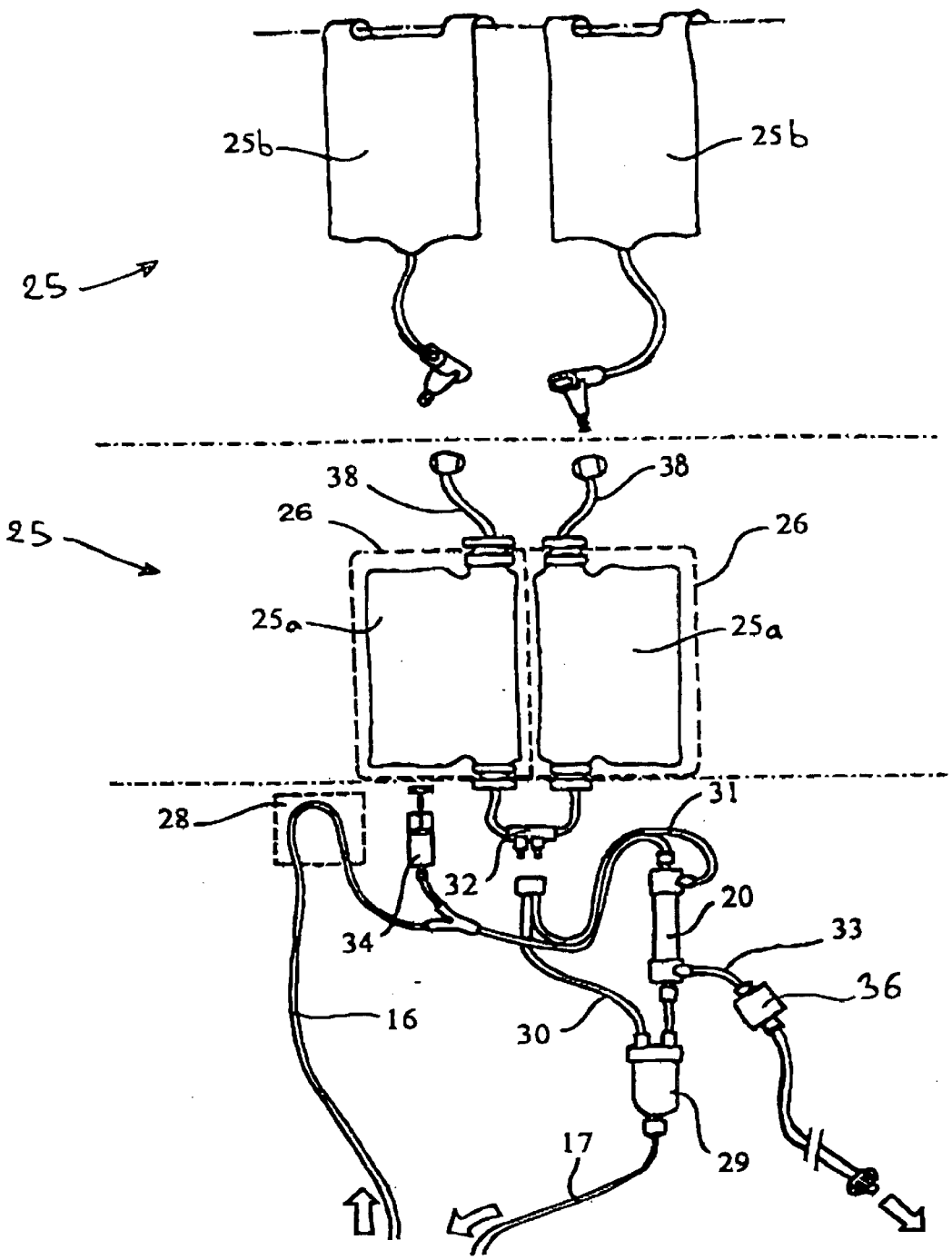

We will describe in detail the two preferred embodiments of dialysis machine 10 of the invention corresponding respectively to chronic dialysis, with particular reference to FIGS. 2A and 3A, and acute dialysis, with particular reference to FIGS. 2B and 3B. Identical components in these two embodiments bear the same reference numerals in the drawings. Dialysis machine 10 consists primarily of the following components:

- a dialyzer 20 of the hollow fiber type with a first inlet 21 and a first outlet 22, a second inlet 23 and a second outlet 24;
- a dialysate supply means 25 which will be described in more detail below;
- at least one chamber 26 capable of pressurization using a gas such as nitrogen or compressed air represented symbolically by arrow B, said chamber containing at least partially said dialysate supply means 25;
- a recovery container 27 for expelled dialysate;
- the arterial line 16 connecting the arteriovenous fistula implanted in the forearm 18 of patient 19 to the first inlet 21 of the dialyzer 20;
- a peristaltic pump 28 attached to the arterial line 16 to generate circulation of the patient's blood through dialyzer 20, acting as a filter;
- the venous line 17 connected to said arteriovenous fistula implanted in the forearm 18 of patient 19 and to the outlet of a bubble trap 29, the first inlet 29a of which is connected to the first outlet 22 of dialyzer 20;
- a dialysate inlet line 31 connected between a collector or a separator 32 joined to said dialysate supply means 25 and the second inlet 23 of dialyzer 20;
- an evacuation line 33 which connects the second outlet 24 of dialyzer 20 to the collection container 27;
- a plunge syringe 34 or other equivalent automatic device which contains medication such as an anticoagulant, for example, and connected with a shunt to arterial line 16;
- a reservoir of gas 35 such as a bottle of nitrogen (see FIG. 5) or an air compressor to pressurize the interior of chamber 26 and consequently the sterile dialysate supply means 25;
- a volumetric device 36, preferably a dialysate pump, connected to the evacuation line 33; and
- a used dialysate drip dispenser 37, shown schematically by arrow C.

Dialysate inlet line 31 leading to dialyzer 20 comprises a major flow restrictor which generates loss of charge. This loss of charge allows regulation of the dialysate flow. This restrictor preferably consists of a reinforced calibrated tube, constant in section, with a narrowed area extending along a relatively long predetermined portion.

Because this restriction extends along a large portion of the tube, it stabilizes flow and eliminates disparities that could occur due to imperfections in tube extrusion.

Dialysis machine 10 designed for chronic dialysis, FIGS. 2A and 3A, comprises a single chamber 26 in the example shown. The exact duration of the intervention and the precise amount of dialysate required are known. Given the relatively small quantity of dialysate, ranging from 25–30 liters, chamber 26 can be designed to hold the entire amount necessary for dialysis. In the example shown sterile dialysate supply means 25 comprises six flexible pouches 25a of relatively small capacity, perhaps 5 liters each, located inside chamber 26 and connected to collector 32 joined to dialysate inlet line 31. The pressure inside chamber 26 is applied directly to pouches 25a and the chamber is maintained at an appropriate temperature for sterile dialysate, generally 37° C.

In acute dialysis, FIGS. 2B and 3B, treatment is continuous and may last several weeks. The dialysate must be permanently available. For this purpose dialysis machine 10 comprises, in the example shown, two chambers 26 which can be separately pressurized with pressurizing means 35 shown symbolically by two arrows B. The sterile dialysate supply means 25 comprises first, two flexible pouches 25a of relatively small capacity (for example, 5 liters each), each respectively disposed inside chamber 26, and coupled by means of collector 32, and also two pouches 25b of relatively small capacity (for example, 5 liters each), located outside chamber 26, each respectively connected to pouch 25a by a connecting conduit 38. Pouches 25b constitute a reserve and are held by a support integral with frame 11. Said support consists of cover 13 to machine 10.

This particular arrangement facilitates manipulation and eliminates the need to open chambers 26, which may be pressurized. Pouches 25a actually remain inside their chamber and are replenished from pouches 25b which are outside the chamber and which are replaced regularly, perhaps by a nurse. The placement of pouches 25a in the chambers allows them to be alternately refilled from reserve pouches 25b by simple gravity, using the system for alternately pinching the conduits, called clamps, and the alternate depressurization of one of the pouches, to successively and alternately fill pouches 25a from pouches 25b holding the reserve. This system continuously supplies dialysate inlet line 31 from one the of pouches 25a located inside pressurized chamber 26.

Dialysis machine 10 as described above for use in chronic dialysis can be configured for use with a technique known as hemodiafiltration, in which sterile dialysate is used both as a liquid exchange for blood at the level of dialyzer 20, and as a substitute liquid introduced directly into the patient's circulatory system. For this purpose collector 32 connected with sterile dialysate pouches 25a is joined through an inlet line 30 for substitute liquid (that is, sterile dialysate) to a second inlet 29b of bubble trap 29, the outlet of which is connected to venous line 17 joined to the arteriovenous fistula implanted in the forearm 18 of the patient 19. Note that this inlet line 30 can remain in place on dialysis machine 10. It is blocked by a device (not shown in the drawings) currently called a clamp when the machine is not being used for hemodiafiltration.

In order to limit the number of electronic controls and retain the simplicity and reliability of dialysis machine 10, the principal tubes, that is lines 30 and 31, which respectively join supply sterile dialysate means 25 to bubble trap 29 and to dialyzer 20 are precisely calibrated so the correct flow rate for a predetermined pressure in chamber 26 is known absolutely.

In the hemodiafiltration procedure, during the dialysis period, or for about 2½ hours, line 31 delivers about 25 liters of dialysate and line 30 delivers about 5 liters of substitute liquid into venous line 17 in patient 19. This method improves the blood purification process due to high convection.

Dialysis machine 20 circulates a large quantity of water through dialyzer membrane 20, possibly 1 to 2 liters per day, which the patient cannot eliminate. This is accomplished using dialysate pump 36, which is a pump with an adjustable flow rate, and which in combination with the means 35 for pressurizing chamber 26 generates a predetermined trans-membrane pressure (TMB), that is, the difference between blood circulation pressure and the pressure of the dialysate in dialyzer 20. This trans-membrane pressure is adjusted so as to eliminate the necessary amount of water.

Trans-membrane pressure also depends upon the loss of charge in the dialysis membrane used and the loss of charge in dialysate inlet line 31 which is connected between pouches 25a inside chamber 26 and dialyzer 20. The loss of charge in line 31 is imperative so water can more readily pass through the membrane under the effect of trans-membrane pressure than the dialysate passes from pouches 25a toward dialyzer 20. In other words, a sufficient loss of charge is created in line 31 so that whatever trans-membrane pressure is generated by dialysate pump 36 and whatever the interior pressure is on the dialysate in chamber 26, the necessary extra dialysate can flow only from the membrane and not from chamber 26. There must be sufficient pressure in chamber 26 for the dialysate to flow at a rate of from 100 to 500 ml/minute through line 31, preferably between 100 and 250 ml/minute, and advantageously of the order of 150 ml/minute. During hemodiafiltration the 5 liters of sterile dialysate injected in venous line 17 are taken from the dialysate side by creating appropriate trans-membrane pressure, for example, by creating depressurization using dialysate pump 36. Said dialysate pump is a volumetric device that is completely dependable for performing this operation.

Figure 5:
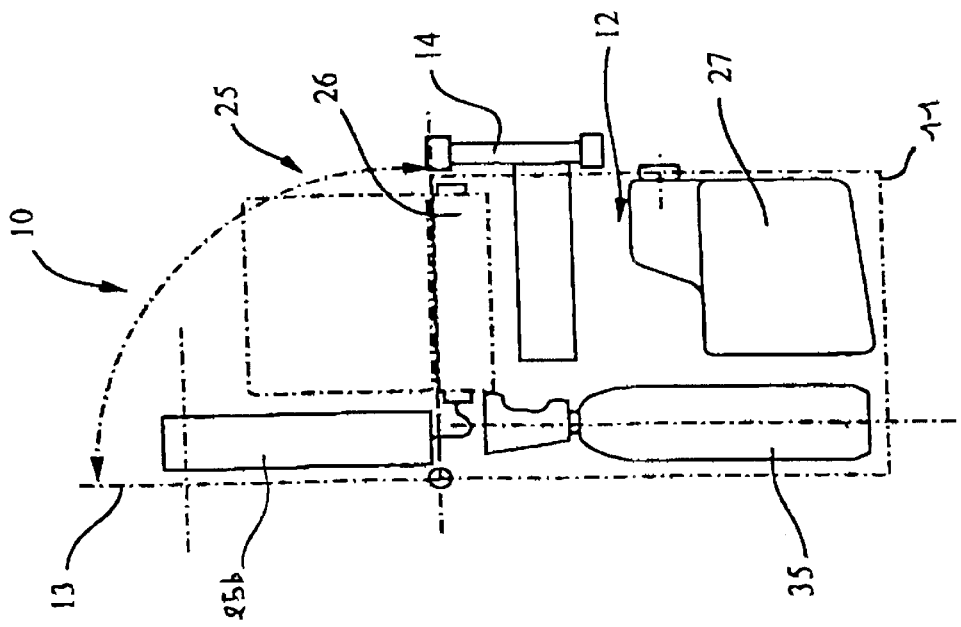
FIGS. 4 and 5 are a front elevation and a lateral elevation, respectively, of the machine according to the invention, with a schematic representation of the arrangement of its essential components.
Figure 4:
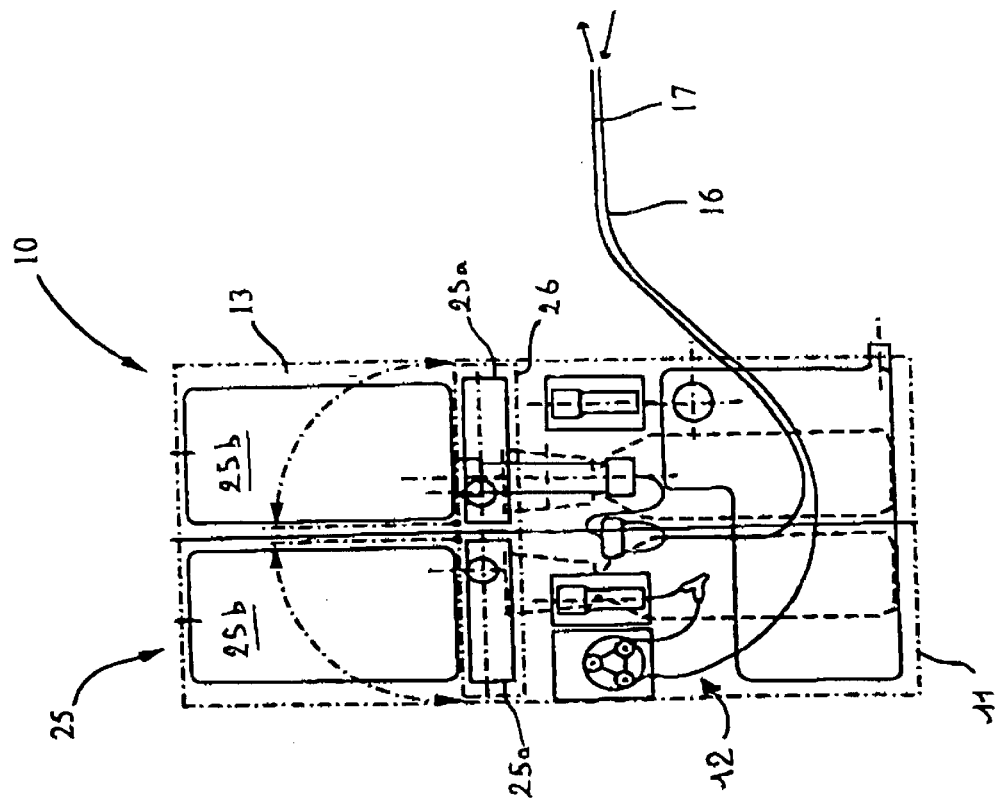

Most components of the machine are located in housing 12 on frame 11, as shown in FIGS. 4 and 5. During acute dialysis, cover 13 of machine 10 is removed during use and reserve pouches 25b are suspended vertically. An electronic control device is also located inside housing 12. It is connected to control panel 14, also shown in FIG. 1.

Dialysis machine 10 may also include a weighing means to determine ultrafiltration of the patient according to one of the following known methods, wherein:

$P_1$ is the weight of the dialysate measured by the weighing means at the dialyzer inlet;

$P_2$ is the weight of the dialysate measured at the dialyzer outlet; and

UF is the patient's ultrafiltration.

a)

the patient's ultrafiltration is determined by the equation $UF = \Delta P = P_2 - P_1$ b)

$P_1 + P_2$ are measured at time $t_1$, for example, at the beginning of dialysis;

$P_1 + P_2$ are measured at time $t_2$, for example, at the end of dialysis;

then the patient's ultrafiltration is calculated, being equal to the difference of the sums $P_1 + P_2$ at the beginning and at the end of dialysis $UF = (P_1 + P_2)_{t2} - (P_1 + P_2)_{t1}$ These weights allow dialysis to be simply and safely controlled either during the treatment session or at the end.

The dialysis machine can be adapted to various uses such as, for example, acute dialysis or chronic dialysis, as previously mentioned, and also automatic peritoneal dialysis. The size and shape of the machine are not limited to what is shown in the drawings. A simple, reliable electronic control system is an essential component to allow the patient to easily practice risk-free auto-dialysis on a daily basis.

The features of this machine are its simple design and reliable operation, making it economical and dependable. In addition, it is very versatile and can be used in all modes of dialysis: hemodialysis, hemodiafiltration, pre- or post-dilution hemofiltration.

What is claimed is:

1. A dialysis machine comprising a dialyzer with a first blood circulation inlet and a first blood circulation outlet, a dialysate supply means, an arterial line connected between an arteriovenous fistula in a patient and the first dialyzer inlet, a venous line connected between the arteriovenous fistula and the first dialyzer outlet, a pump coupled with the arterial line, a dialysate inlet line connected between the dialysate supply means and a second dialyzer inlet, and a dialysate evacuation line connected between a dialysate collection container and a second dialyzer outlet, wherein the dialysate supply means (25) includes at least two chambers (26), each of the at least two chambers containing at least one primary pouch (25a) of sterile dialysate, each of the at least one primary-pouches (25a) connected to the dialysate inlet line (31) leading to the dialyzer (20), pressurizing means for separately pressurizing each of the at least one primary pouches (25a) to provoke the flow of dialysate into the inlet line (31), each of the at least two chambers further containing at least one reserve pouch (25b) of sterile dialysate, with each of the at least one reserve pouches (25b) connected by a conduit (38) to a primary pouch (25a) within each of the at least two chambers (26), the dialysate inlet line (31) including a flow restrictor for generating a predetermined decrease in charge calculated so that for a given pressure in each of the at least two chambers (26), the flow rate and the pressure of the dialysate at the second inlet (23) on the dialyzer (20) have a constant given value, the dialysis machine including a volumetric device (36) connected to the evacuation line (33) at the second outlet (24) of the dialyzer (29), the volumetric device (36) designed to generate, in combination with the means for pressurizing the at least one primary pouch (25a) within each of the at least two chambers (26), a predetermined trans-membrane pressure in the dialyzer.

2. The dialysis machine according to claim 1, further comprising means for alternately clamping the conduits (38).

3. The dialysis machine according to claim 1, further comprising a frame (11) with a housing (12) containing the dialyzer (20), a folding cover (13) attached to the frame (11), the arterial line (16) located so it can be connected between an artery of the patient (19) and the first inlet (21 of the dialyzer (20), the venous line (17) located so it can be connected between a vein of the patient (19) and the first outlet (22) of the dialyzer (20), and the pressurizing means housed within said chamber (26).

4. The dialysis machine according to claim 1, wherein the housing (12) encloses the at least two chambers (26), and further includes a support integral with the frame (11) which holds the reserve pouches (25b).

5. The dialysis machine according to claim 4, wherein the support for the reserve pouches (25b) includes the cover (13).

6. A dialysis machine comprising a dialyzer with a first blood circulation inlet and a first blood circulation outlet, a dialysate supply means, an arterial line connected between an arteriovenous fistula in a patient and the first dialyzer inlet, a venous line connected between the arteriovenous fistula and the first dialyzer outlet, a pump coupled with the arterial line, a dialysate inlet line connected between the dialysate supply means and a second dialyzer inlet, and a dialysate evacuation line connected between a dialysate collection container and a second dialyzer outlet, the dialysate supply means including sterile dialysate contained in at least one pouch (25a), each at least one pouch connected by the dialysate inlet line (31) to the dialyzer (20), and means for pressurizing the pouch (25a) to provoke the flow of dialysate into the inlet line (31), wherein the supply means includes at least two chambers each containing at least one pouch of sterile dialysate, each of said pouches capable of separate pressurization.

7. The dialysis machine according to claim 5, further comprising at least one reserve pouch (25b) of sterile dialysate located outside each of the at least two chambers (26), each of the at least-one reserve pouches (25b) connected to one of the pouches (25a) by a conduit (38).

8. The dialysis machine according to claim 6, wherein the dialysate inlet line (31) has a flow restrictor for generating a predetermined decrease in charge calculated so that for a given pressure in the chamber (26) the flow rate and the pressure of the dialysate at said second inlet (23) on the dialyzer (20) have a constant value.

9. The dialysis machine according to claim 6, further comprising a volumetric device (36) connected to the evacuation line (33) at the second outlet (24) of the dialyzer (20), the volumetric device (36) capable of generating, in combination with the pressurizing means, a predetermined trans-membrane pressure in the dialyzer.

10. The dialysis machine according to claim 7, further comprising means for alternately clamping the conduits (38).

11. The dialysis machine according to claim 6, wherein the dialysate inlet line (31) leading to the dialyzer (20) is calibrated so that for a predetermined pressure in the chamber (26) the dialysate will flow at a rate ranging from about 100 to about 500 ml/minute.

12. The dialysis machine according to claim 11, wherein the dialysate inlet line (31) leading to the dialyzer (20) is calibrated so that for a predetermined pressure in the chamber (26) the dialysate will flow at a rate ranging from about 100 to about 250 ml/minute.

13. The dialysis machine according to claim 6, wherein the dialysate inlet line (31) consists at least partially of a reinforced calibrated tube of constant cross-section for a predetermined length.

14. The dialysis machine according to claim 6, wherein the pressurization means maintains an interior pressure within the chamber (26) that is sufficient to provoke the flow of dialysate through the inlet lines (30, 31), respectively, to a bubble trap (29) and to the dialyzer (20).

15. The dialysis machine according to claim 6, wherein the dialysate inlet lines (30, 31) are calibrated so that for a predetermined pressure in the chamber (26) flow rates within the inlet lines (30, 31) will have a constant given value.

16. The dialysis machine according to claim 10, wherein the volumetric device (36) is a dialysate pump with an adjustable rate of flow.

17. The dialysis machine according to claim 6, further comprising a frame (11) with a housing (12) containing the dialyzer (20), a folding cover (13) attached to the frame (11), the arterial line (16) located such that it can be connected between an artery of a patient (19) and the first inlet (21) of the dialyzer (20), the venous line (17) located so it can be connected between a vein of the patient (19) and the first outlet (22) of the dialyzer (20), and the pressurizing means is housed within the chamber (26).

18. The dialysis machine according to claim 17, wherein the housing (12) encloses each of the at least two chambers (26).

19. The dialysis machine according to claim 7, further comprising a support integral with the frame (11), which holds the reserve pouches (25*b*) of sterile dialysate.

* * * * *